US009138331B2

(12) United States Patent
Aferzon (10) Patent No.: US 9,138,331 B2
(45) Date of Patent: Sep. 22, 2015

(54) ANTERIOR INTERVERTEBRAL FUSION WITH FIXATION SYSTEM, DEVICE, AND METHOD

(71) Applicant: Joshua Michael Aferzon, Stamford, CT (US)

(72) Inventor: Joshua Michael Aferzon, Stamford, CT (US)

(*) Notice: Subject to any disclaimer, the term of this patent is extended or adjusted under 35 U.S.C. 154(b) by 0 days.

(21) Appl. No.: 14/492,160

(22) Filed: Sep. 22, 2014

(65) Prior Publication Data
US 2015/0012102 A1    Jan. 8, 2015

Related U.S. Application Data

(63) Continuation of application No. 13/371,242, filed on Feb. 10, 2012, now abandoned.

(60) Provisional application No. 61/517,717, filed on Apr. 25, 2011, provisional application No. 61/463,239, filed on Feb. 15, 2011.

(51) Int. Cl.
*A61F 2/44* (2006.01)
*A61B 17/16* (2006.01)
(Continued)

(52) U.S. Cl.
CPC ............. *A61F 2/447* (2013.01); *A61B 17/1671* (2013.01); *A61B 17/864* (2013.01); *A61B 17/8875* (2013.01); *A61F 2/442* (2013.01); *A61F 2002/2835* (2013.01);
(Continued)

(58) Field of Classification Search
CPC ......... A61F 2/44; A61F 2/442; A61F 2/4455; A61F 2/447; A61F 2002/2835; A61F 2002/30266; A61F 2002/30326; A61F 2002/30835

USPC ............................................. 623/17.11–17.16
See application file for complete search history.

(56) References Cited

U.S. PATENT DOCUMENTS 4,320,544 A * 3/1982 Bryant et al. .................... 7/158
5,098,435 A * 3/1992 Stednitz et al. ............... 606/916
(Continued)

FOREIGN PATENT DOCUMENTS

WO    WO 2007098288 A2 *   8/2007 ................ A61F 2/44

OTHER PUBLICATIONS

International Search Report dated Jun. 6, 2012, issued in EP Application No. PCT/US2012/24791, mailed on Jun. 20, 2012.
(Continued)

*Primary Examiner* — Christian Sevilla
*Assistant Examiner* — Eric S Gibson
(74) *Attorney, Agent, or Firm* — The Marbury Law Group, PLLC (57) ABSTRACT

A system, device, and method are disclosed for anterior intervertebral fusion with fixation. An intervertebral fusion with fixation device includes a spacer configured to fit into a disc space between plural vertebrae, the spacer including through holes between and through plural sidewalls. A first fixating element is rigidly preloaded in a first portion of the spacer along a first linear trajectory. A second fixating element is rigidly preloaded in a second portion of the spacer along a second linear trajectory. An integrated drill and screwdriver instrument is adapted to extend through a cannula of the first fixating element and second fixating element and penetrate the vertebra. The instrument is further adapted to drive the head of the first fixating element and second fixating element into the vertebra and lock the first fixating element and second fixating element with respect to the spacer to prevent extrusion from the spacer.

13 Claims, 8 Drawing Sheets

(51) Int. Cl.
*A61B 17/86* (2006.01)
*A61B 17/88* (2006.01)
*A61F 2/28* (2006.01)
*A61F 2/30* (2006.01)

(52) U.S. Cl.
CPC *A61F 2002/3008* (2013.01); *A61F 2002/3023* (2013.01); *A61F 2002/30266* (2013.01); *A61F 2002/30326* (2013.01); *A61F 2002/30787* (2013.01); *A61F 2002/30835* (2013.01); *A61F 2002/30879* (2013.01)

(56) References Cited

U.S. PATENT DOCUMENTS

| | | | |
|---|---|---|---|
| 5,242,444 | A | 9/1993 | MacMillan |
| 5,645,547 | A * | 7/1997 | Coleman ............... 606/304 |
| 6,503,279 | B1 * | 1/2003 | Webb et al. ............ 623/17.16 |
| 6,843,805 | B2 * | 1/2005 | Webb et al. ............ 623/17.16 |
| 7,041,105 | B2 | 5/2006 | Michelson |
| 7,238,203 | B2 | 7/2007 | Bagga et al. |
| 7,442,209 | B2 | 10/2008 | Michelson |
| 7,604,643 | B2 * | 10/2009 | Ciccone et al. ............ 606/104 |
| 7,621,957 | B2 * | 11/2009 | Errico et al. ............ 623/17.16 |
| 7,662,183 | B2 * | 2/2010 | Haines ................... 623/17.11 |
| 7,846,207 | B2 | 12/2010 | Lechmann et al. |
| 8,419,797 | B2 * | 4/2013 | Biedermann et al. ...... 623/17.16 |
| 2003/0125749 | A1 * | 7/2003 | Yuan et al. ............ 606/104 |
| 2007/0055257 | A1 | 3/2007 | Vaccaro et al. |
| 2007/0225813 | A1 * | 9/2007 | Haines ................... 623/17.16 |
| 2007/0239159 | A1 | 10/2007 | Altarac et al. |
| 2008/0234758 | A1 | 9/2008 | Fisher et al. |
| 2009/0030520 | A1 * | 1/2009 | Biedermann et al. ...... 623/17.16 |
| 2009/0210062 | A1 | 8/2009 | Thalgott et al. |
| 2009/0234455 | A1 | 9/2009 | Moskowitz et al. |
| 2009/0287249 | A1 * | 11/2009 | Reynolds et al. ............ 606/246 |
| 2010/0057206 | A1 * | 3/2010 | Duffield et al. ............ 623/17.16 |
| 2010/0161057 | A1 * | 6/2010 | Berry et al. ................. 623/17.16 |
| 2010/0168798 | A1 | 7/2010 | Clineff et al. |
| 2010/0217393 | A1 | 8/2010 | Theofilos |
| 2010/0305704 | A1 * | 12/2010 | Messerli et al. ............ 623/17.16 |
| 2010/0312346 | A1 * | 12/2010 | Kueenzi et al. ............ 623/17.16 |
| 2011/0015745 | A1 | 1/2011 | Bucci |
| 2011/0166656 | A1 * | 7/2011 | Thalgott et al. ............ 623/17.16 |
| 2011/0166657 | A1 * | 7/2011 | Thalgott et al. ............ 623/17.16 |
| 2011/0196493 | A1 * | 8/2011 | Pimenta .................... 623/17.16 |
| 2011/0230969 | A1 * | 9/2011 | Biedermann et al. ...... 623/17.16 |
| 2011/0313528 | A1 * | 12/2011 | Laubert et al. ............. 623/17.16 |
| 2012/0209385 | A1 * | 8/2012 | Aferzon .................... 623/17.16 |
| 2012/0277873 | A1 * | 11/2012 | Kana et al. ............... 623/17.16 |
| 2012/0316649 | A1 * | 12/2012 | Johnston et al. ........... 623/17.16 |
| 2012/0323330 | A1 * | 12/2012 | Kueenzi et al. ............ 623/17.16 |
| 2013/0060336 | A1 * | 3/2013 | Hooper et al. ............. 623/17.11 |
| 2013/0166032 | A1 * | 6/2013 | McDonough et al. ..... 623/17.16 |

OTHER PUBLICATIONS

International Preliminary Report on Patentability issue for International Application No. PCT/US2012/024791, mailed on Mar. 20, 2014.

* cited by examiner

ANTERIOR INTERVERTEBRAL FUSION WITH FIXATION SYSTEM, DEVICE, AND METHOD

RELATED APPLICATIONS

This application is a continuation application of U.S. Non-Provisional application Ser. No. 13/371,242 filed Feb. 10, 2012, which claims the benefit of U.S. Provisional Application No. 61/463,239, filed on Feb. 15, 2011, and U.S. Provisional Application No. 61/517,717, filed on Apr. 25, 2011, the entire contents of which is hereby incorporated by reference.

FIELD

The present disclosure relates to spinal implants and associated instrumentation. Various embodiments are directed to an anterior intervertebral fusion with fixation system, device and method.

BACKGROUND

A healthy spinal disc (intervertebral disc) is a fibroelastic structure with a non-compressible viscous center that articulates adjacent vertebrae. Due to its deformable geometry, the disc not only supports normal functional loads of the human body, but also evenly distributes the stresses applied during body movement and positioning. The disc interfaces with associated superior and inferior vertebrae via large surface areas known as vertebral endplates. Normally, vertebral endplates are thin regions of dense bone (e.g. 1 mm-3 mm) that support high stresses at articulating junctions.

Intervertebral discs and adjacent articulations progressively deteriorate with age. This natural degenerative process results in various degrees of pathological changes, mostly affecting the geometry and elasticity of a vertebral disc. In severe cases, reduced disc volume results in foraminal compression that mechanically irritates nerve roots and causes neurocompressive syndrome. This often causes severe chronic pain that can only be resolved surgically.

Historically, surgical treatment of degenerative spinal disc disease required fusion, which immobilizes two adjacent vertebral bodies (vertebrae) to prevent motion-sensitive pain and inflammation. This is accomplished by distracting the vertebrae to a healthy disc height, inserting a disc implant and allowing bone to grow between and through the disc implant until the vertebrae fuse into a solid bony structure. To facilitate proper healing under normal conditions of motion, the disc implant is used to maintain temporary positioning until the bone achieves fusion. The implant is secured to the vertebrae using fixation elements.

The effectiveness of the disc implant can be evaluated with the following criteria: (i) its ability to restore and maintain normal disc height and curvature; (ii) its ease of delivery and fixation to the disc space; (iii) its ability to facilitate fusion of associated vertebrae; and (iv) its ability to restrict movement of associated vertebrae.

Disc implants share the same fundamental characteristics to meet the effectiveness criteria. Implants aim to restore disc height through the use of variable geometries. Lordotic curvature is preserved through the use ergonomic designs that conform to spinal curvature and height between the vertebrae. Also, the disc implants are sufficiently porous or hollow to promote the growth of vertebral bone into and through the implant. However, independently, these implants can only restrict spinal flexion and intervertebral compression. Any excessive lateral, sliding, or extension motion may cause device failure and/or extrusion. To avoid this risk, it is customary to provide additional fixation of the disc implant to the vertebrae.

Devices and systems may integrate fixating members directly into the disc implant. These implants have garnered the nickname "standalone" due to their ability to self-fixate without the use of secondary fixation elements. In the foregoing standalone implants, obtrusive fixation elements are delivered directly through implant pilot openings into the vertebra, which fixate the implant to the vertebrae and prevent implant failure under remaining ranges of motion (e.g., lateral, sliding, extension). Nevertheless, during these motions, connectivity between fixation elements and vertebrae may become weakened causing the fixation elements to slip or extrude out of the implant. To prevent unwanted fixation element slipping or extrusion, it is customary to include a locking mechanism for the implant.

SUMMARY

In an embodiment, an intervertebral fusion with fixation device is disclosed. The device includes a spacer with an insertion wall, a trailing wall opposite to the insertion wall, a first lateral wall, a second lateral wall opposite to the first lateral wall, a top surface, and a bottom surface opposite to the top surface. The intervertebral fusion with fixation device further includes a first fixating element rigidly preloaded in a first portion of the spacer along a first linear trajectory, the first fixating element configured to penetrate and secure to a first vertebra by advancing along the first linear trajectory. The device also includes a second fixating element rigidly preloaded in a second portion of the spacer along a second linear trajectory that is different from the first linear trajectory, the second fixating element configured to penetrate and secure to a second vertebra by advancing along the second trajectory. Further, the intervertebral fusion with fixation device includes a through opening having an entrance proximate the top surface and an exit proximate the bottom surface to facilitate contact and in-growth of bone fusion material with the first vertebra and second vertebra.

In another embodiment, an integrated drill and screwdriver instrument is disclosed. The integrated drill and screwdriver includes a handle, a driving element configured to engage a head of a bone screw and rotate the bone screw into a vertebra, and a drilling element extending from the from the driving element. The drilling element is configured to extend through a cannula of the bone screw and to penetrate the vertebra. The driving element is configured to engage the head of the bone screw as the drilling element penetrates through a vertebral endplate.

In a further embodiment, an intervertebral fusion with fixation system is disclosed. The system includes an intervertebral fusion with fixation device configured to be implanted between plural vertebrae. The device includes a spacer with an insertion wall, a trailing wall opposite to the insertion wall, a first lateral wall, a second lateral wall opposite to the first lateral wall, a top surface, and a bottom surface opposite to the top surface. The device further includes a first fixating element rigidly preloaded in a first portion of the spacer along a first linear trajectory, the first fixating element configured to penetrate and secure to a first vertebra by advancing along the first linear trajectory. Additionally, the device also includes a second fixating element rigidly preloaded in a second portion of the spacer along a second linear trajectory that is different from the first linear trajectory, the second fixating element configured to penetrate and secure to a second vertebra by advancing along the second trajectory. The system also includes an integrated drill and screwdriver instrument. The integrated instrument includes a handle, a driving element configured to engage a head of a bone screw and rotate the bone screw into a vertebra, and a drilling element extending from the from the driving element. The drilling element is configured to extend through a cannula of the bone screw and to penetrate the vertebra. The driving element is configured to engage the head of the bone screw as the drilling element penetrates through a vertebral endplate.

In yet another embodiment, a method to secure plural vertebrae is disclosed. The method includes implanting an intervertebral fusion with fixation device between plural vertebrae. The fusion with fixation device includes a spacer, a first fixating element rigidly preloaded in a first portion of the spacer along a first linear trajectory, and a second fixating element rigidly preloaded in a second portion of the spacer along a second linear trajectory that is different from the first linear trajectory. The method further includes driving the first fixating element along the first linear trajectory to penetrate the first vertebra and to secure the spacer to a first vertebra, and driving the second fixating element along the second linear trajectory to penetrate the second vertebra and to secure the spacer to a second vertebra. The method also includes extending an integrated drill and screwdriver instrument through a cannula of the first fixating element and a cannula of the second fixating element, drilling the plural vertebrae with a drilling element, engaging the first fixating element and second fixating element with a driving element as the drilling element penetrates through a vertebral endplate of the plural vertebrae, and rotating the first fixating element and second fixating element via the driving element to penetrate the plural vertebrae and to secure the spacer to the plural vertebrae. The method further includes locking the first fixation element and second fixation element with respect to the spacer to prevent the first fixation element and second fixation element from extruding from the plural vertebrae and from the spacer.

In a further embodiment, a method to assemble an intervertebral fusion with fixation device is disclosed. The method includes rigidly preloading a first fixating element in a first portion of a spacer along a first linear trajectory and a second fixating element in a second portion of the spacer along a second linear trajectory, the first linear trajectory being different from the second linear trajectory.

DETAILED DESCRIPTION

Figure 1:
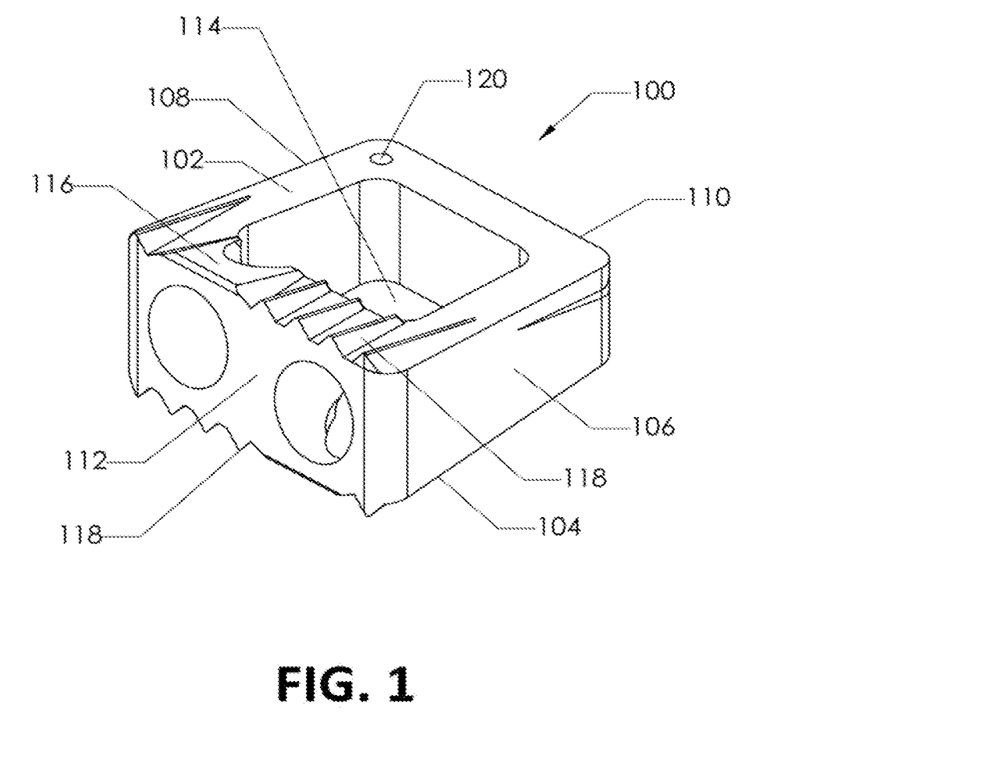
FIG. 1 is a perspective view of an example spacer of an intervertebral fusion with fixation device.
Figure 8:
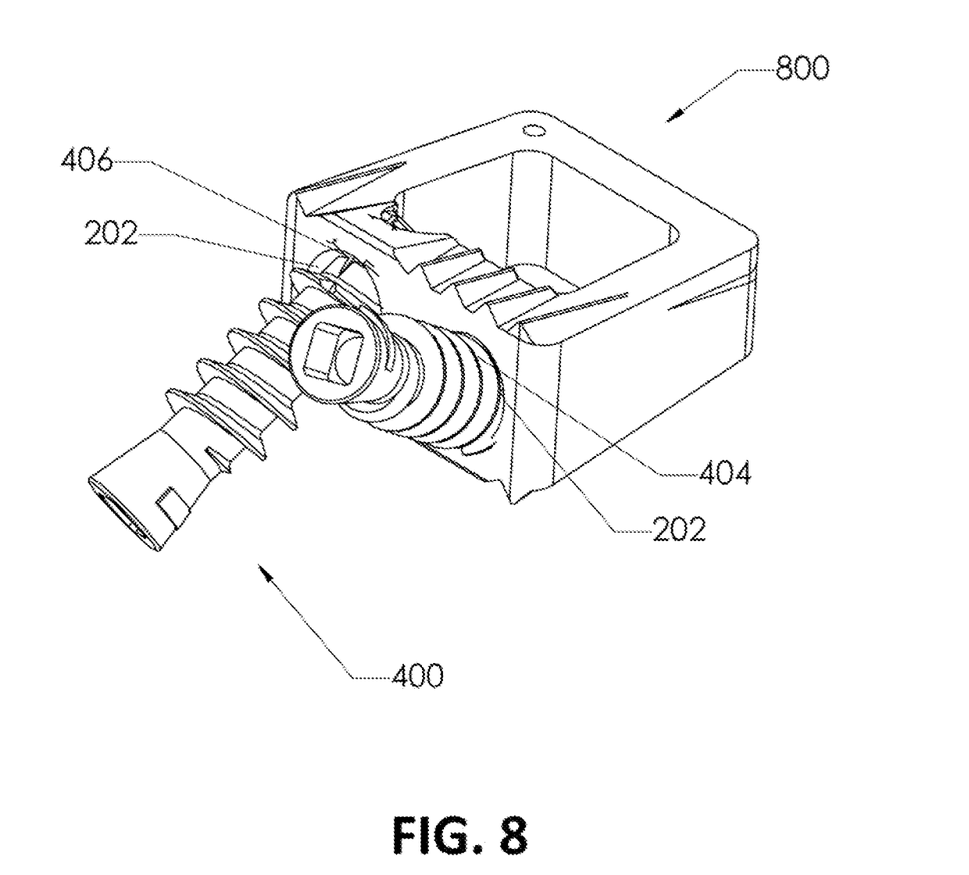
FIG. 8 is a perspective view of an example intervertebral fusion with fixation device with the example fixation elements shown in FIG. 4 preloaded in the example spacer shown in FIG. 1.

FIG. 1 is a perspective view of an example spacer 100 of an intervertebral fusion with fixation device. The intervertebral fusion with fixation device is illustrated in FIG. 8. The spacer 100 is made of a weight-bearing material, such as a polymer, metal, ceramic, biological material, or composite thereof, that is capable of withstanding the normal stresses of bodily movement and positioning, while also allowing sufficient elasticity. The material can have a flexural modulus and tensile strength comparable to bone. For example, the spacer 100 can be made of polyetheretherketone (PEEK), a thermoplastic with a flexural modulus of 4.2 GPa and a tensile strength of 95 MPa. Another benefit of PEEK is its high level of biocompatibility in a dynamic and immunoreactive environment. Other materials and combinations of materials are possible.

The spacer 100 includes an insertion wall 110, trailing wall 112, lateral walls 106, 108, top surface 102, bottom surface 104, and through opening 114 extending between and through the top surface 102 and bottom surface 104 for bone graft insert.

In various embodiments, the dimensions of the spacer 100 are approximately the following: the length of the spacer 100 between an insertion wall 110 and trailing wall 112 is between about 10 mm and 80 mm; the width of the spacer 100 between a first lateral wall 106 and second lateral wall 108 is between about 10 mm and 80 mm; and the height of the spacer 100 between a top surface 102 and bottom surface 104 is between about 4 mm and 30 mm. The foregoing dimensions are non-limiting and are intended to be adjusted depending on the specific spinal anatomy of the patient.

The opening 114 can have a volume approximately between 0 cm3 and 8 cm3. Other volumes can be provided. While the insertion wall 110, trailing wall 112, and lateral walls 106, 108 are generally flat surfaces, the top surface 102 and bottom surface 104 may be tapered or curved with respect to one another to conform to intervertebral lordosis or curvature. The lateral walls 106, 108 can also have a tapered geometry to conform to intervertebral space. In some embodiments, the angle between the lateral surfaces 106, 108 can be from about 0 degrees to about 16 degrees.

Figure 4:
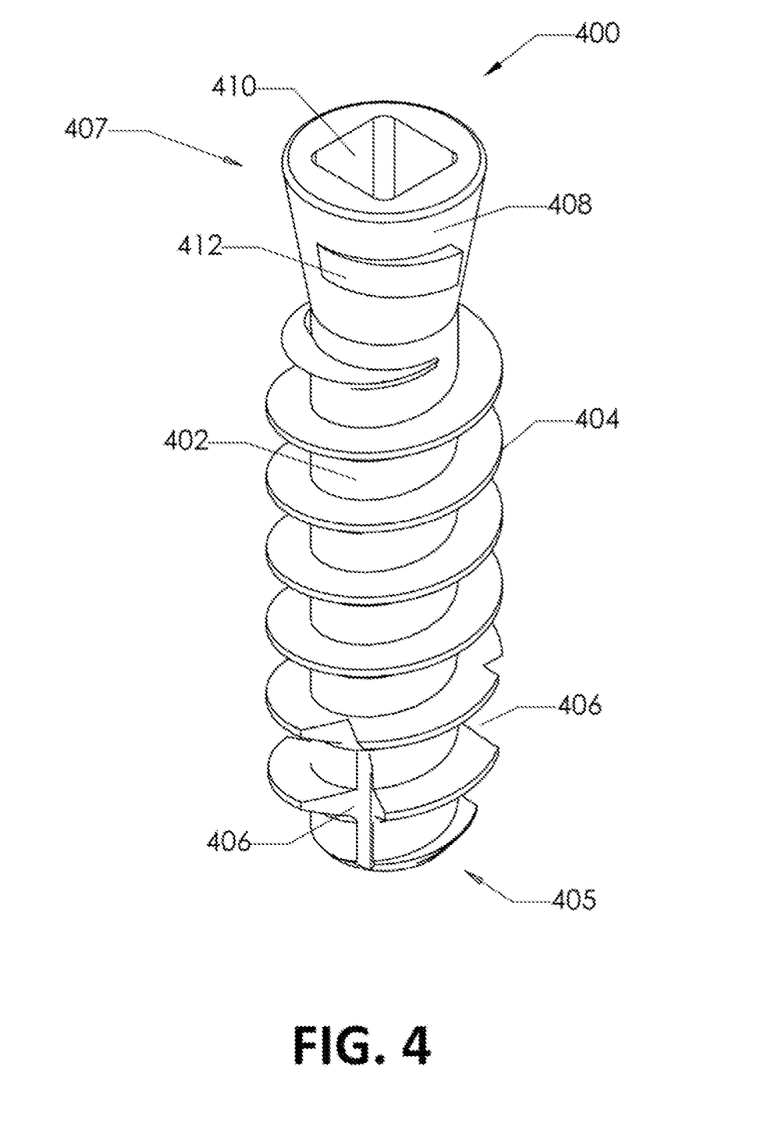
FIG. 4 is a perspective view of an example fixation element of the intervertebral fusion with fixation device.

The trailing wall 112 includes a plurality of through holes 202 (shown in FIG. 2) extending from the central opening 114 to the exterior of the spacer 100 to receive, secure, and guide plural fixation elements 400 (shown in FIG. 4). Each of the foregoing holes 202 is oriented to provide a trajectory for a fixation element (shown in FIG. 4). The trajectories of the holes 202 can be oriented in directions lateral, medial, superior, inferior, or any combination thereof to the spacer to provide multi-axial fixation to the vertebrae. In some embodiments, the holes 202 can direct the fixation elements 400 in divergent trajectories to counterbalance one another from any opposing torques or shear stresses initiated by vertebral motion. The dimensions of the holes 202 are approximately the following: the medial and/or lateral angle in respect to lateral walls 106, 108 is between about 0 degrees and 25 degrees, and the superior and/or inferior angle in respect to surfaces 102, 104 is between about 30 degrees and 50 degrees. The diameters of the foregoing holes 202 are approximately between 0.5 mm and 10 mm.

Figure 2:
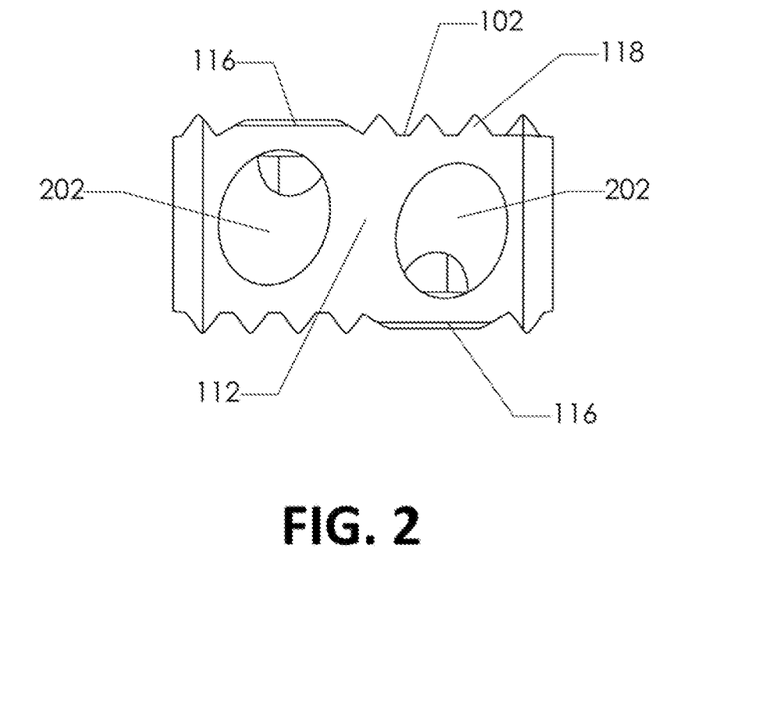
FIG. 2 is a front view of the example spacer shown in FIG. 1.

FIG. 2 is a front view of the example spacer 100 shown in FIG. 1. Now with reference to FIGS. 1 and 2, the spacer 100 includes ridges 116 on surfaces 102, 104 proximate the holes 202 to reinforce the spacer 100 during advancement of the fixation elements 400. For example, ridges 116 can be provided about the exits to the outside of the spacer 100 and can be of various dimensions and tapers along the surfaces 102, 104. In some embodiments, the ridges 116 can be omitted. The spacer 100 further includes ridges 118 along the surfaces 102, 104 that penetrate surrounding vertebrae during implantation and provide stability to the spacer 100 through microscale contact with the vertebral plates.

The spacer 100 can include plural radiopaque markers 120 to enhance radiographic visualization of the spacer 100. The markers 120 can be made of a biocompatible radiopacic material, such as tantalum, platinum alloys, gold alloys, or palladium alloys. Other applicable materials may also be employed. Plural markers 120 can be provided near the walls 106, 108, 110, 112 and surfaces 102, 104 to provide additional visual references of the spacer 100 for clinicians during radiographic imaging. Furthermore, the markers 120 can assume various geometries and volumes within the spacer 100 depending on visualization requirements. In various embodiments, the markers 120 can be omitted.

Figure 3:
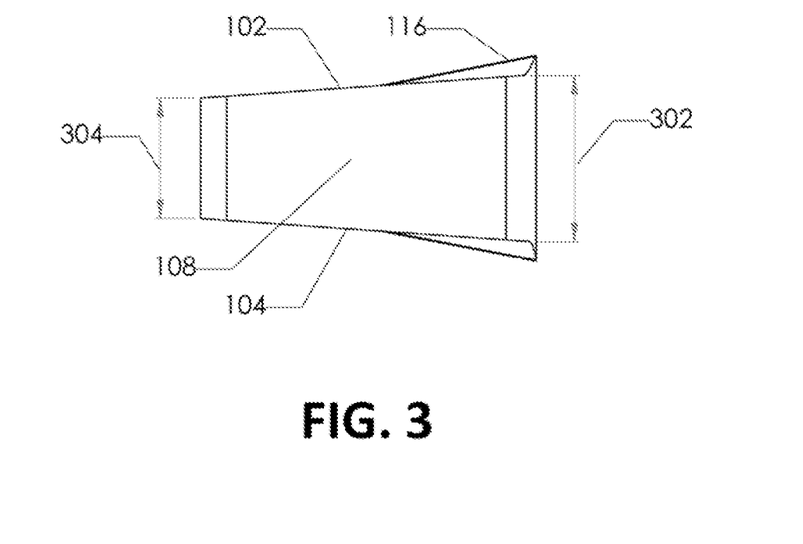
FIG. 3 is a side view of the example spacer shown in FIG. 1.

FIG. 3 is a side view of an example spacer 100 of an intervertebral fusion with fixation device of FIG. 8. In a particular embodiment, the trailing height 302 gradually decreases to the insertion height 304 at a taper to approximate natural lordosis. Additionally, the ridges 116 can be also tapered to minimize friction during insertion and facilitate smooth entry of the spacer 100 into the intervertebral space.

FIG. 4 is a perspective view of an example fixation element 400. In a particular embodiment, the fixation element 400 can be made of a biocompatible metal, such as a titanium alloy. Other applicable materials may also be employed. The fixation element 400 includes a tip 405 that locks into and interfaces with the holes 202 during assembly to maintain a preloaded position, and penetrates bone during engagement with vertebral endplates. The fixation element 400 has a minor diameter 402 that is between about 1 mm and 10 mm. The fixation element 400 also includes a major diameter 404 of threading that is between 2 mm and 15 mm to provide cutting during engagement.

Additionally, the tip 405 includes flutes 406 to facilitate penetration into the vertebra during initial engagement. The fixation element 400 further includes a head 407 with a conically shaped body 408 to pressure-fit into the holes 202 after advancement via an instrument receiver 410. The instrument receiver 410 can interface with a driving instrument (shown in FIG. 6). In a particular embodiment, the head 407 includes a hook protrusion 412 with a sharp edge that can cut into the hole 202 after the fixation element 400 is advanced (e.g., fully) into the vertebra and the head 407 is in contact with the spacer 100. The contact between the sharp edge of the hook protrusion 412 and the hole 202 functions as a locking mechanism to prevent extrusion of the fixation element 400.

Figure 5:
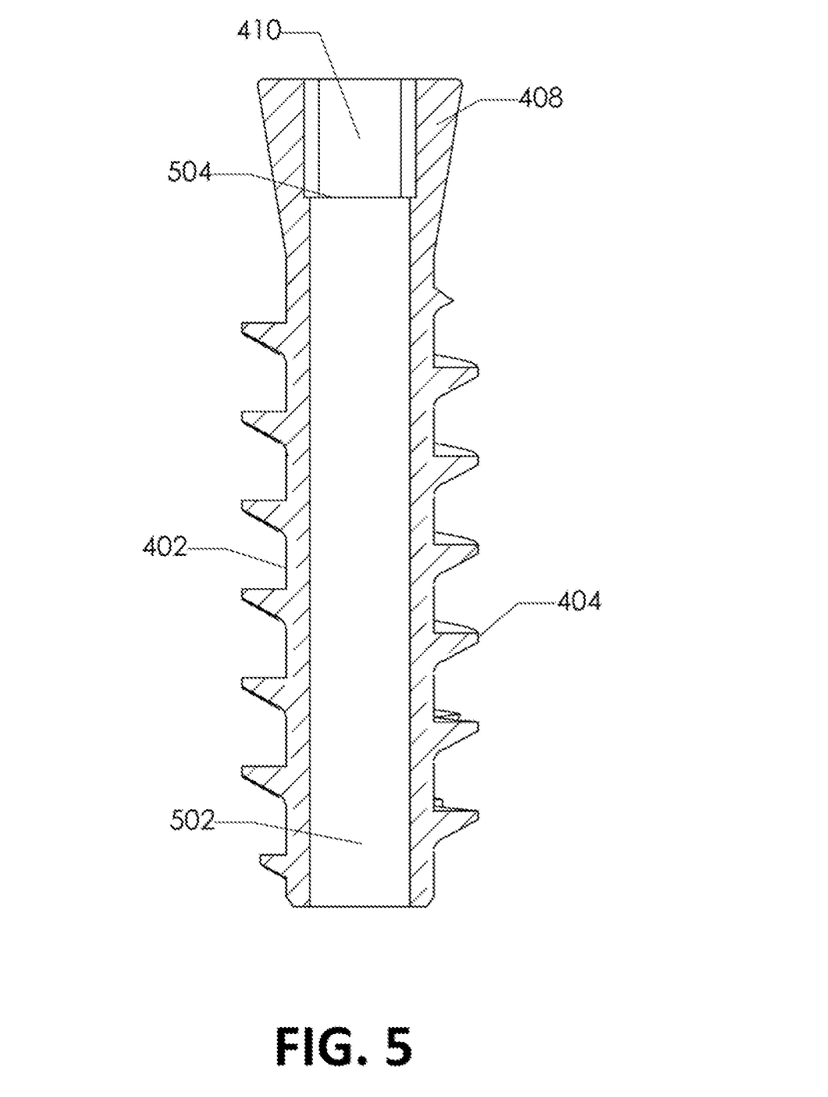
FIG. 5 is a cross-sectional side view of the example fixation element show in FIG. 4.

FIG. 5 is a cross-sectional side view of an example fixation element 400 of FIG. 4. As illustrated, the fixation element 400 includes a cannula 502 that allows a drilling tip of the driving instrument (shown in FIG. 6) to pass into and through the fixation element 400 to facilitate vertebral endplate pre-drilling and preparation for advancement of the fixation element 400. The fixation element 400 further includes a platform 504 that connects or interfaces the driving instrument receiver 410 and cannula 502 to contact and limit the depth of motion of the driving instrument (shown in FIG. 6) in relation to the fixation element 400.

Figure 6:
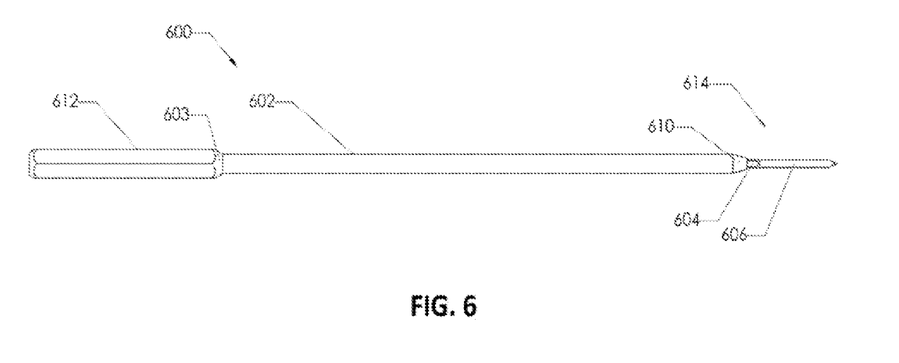
FIG. 6 is a side view of an example integrated drill and screwdriver driving instrument.

FIG. 6 is a side view of an example integrated drill and screwdriver driving instrument (driving instrument) 600. In a particular embodiment, the driving instrument 600 can be made of a metal, such as titanium. Other applicable materials may also be employed. The driving instrument 600 includes an integrated tip 614 that can penetrate and pre-drill vertebral endplates with a drill tip 606 as well as engage the driving instrument receiver 410 of a fixation element 400 with a fixation element interface 604.

The drill tip 606 of the integrated tip 614 can pass into and through the cannula 502 of the fixation element 400 in order to penetrate and pre-drill a vertebral endplate. The fixation element interface 604 can contact the driving instrument receiver 410 once the drill tip 606 has penetrated through the vertebral endplate into the softer bony layer. In a particular embodiment, both the fixation element interface 604 and corresponding driving instrument receiver 410 are of a quadrilateral shape to facilitate rigid contact between the surfaces and allow engagement of the fixation element 400.

The driving instrument 600 includes a body 602 to increase operational distance from the spacer 100 and provide access under various angulations. The body 602 is smoothly mated to the integrated tip 614 with a conical transition element 610. Furthermore, the driving instrument 600 includes a handle 612 that can be operated manually or by an electrical or mechanical tool. In a particular embodiment, the handle 612 can be constructed as a hexagonal bit to fit a standard screwdriver. The handle 612 is smoothly mated to the body 602 with a conical transition element 603.

Figure 7:
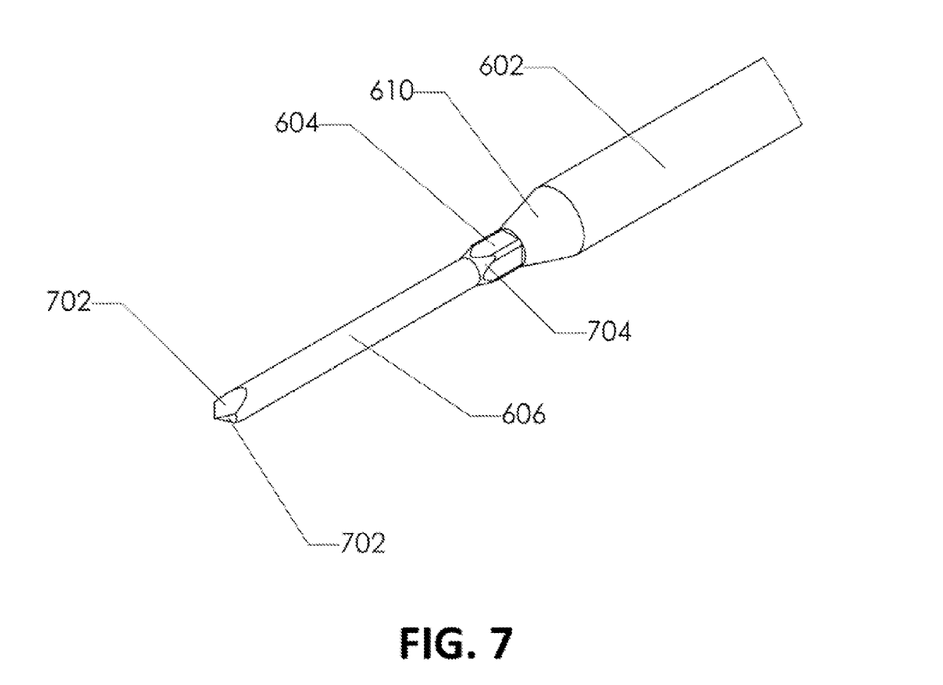
FIG. 7 is a perspective exploded view of a tip of the example integrated drill and screwdriver drilling tip shown in FIG. 6.

FIG. 7 is an exploded perspective view of the example integrated tip 614. The integrated tip 614 includes cutting blades 702 to facilitate vertebral penetration during advancement. The integrated tip 614 further includes a rounded transition element 704 between the fixation element interface 604 and the drill tip 606 to allow smooth contact between the fixation element interface 604 and driving instrument receiver 410 during the initial engagement of the fixation element 400.

FIG. 8 is a perspective view of an example intervertebral fusion with fixation device 800 with the plural example fixation elements 400 of FIG. 4 preloaded in the example spacer 100 of FIG. 1. As illustrated, the fixation elements 400 can be preloaded into the spacer 100 via holes 202. The flutes 406 and threading 404 cut into and secure the fixation elements 400 to the spacer 100 via holes 202 to maintain a preloaded assembly. This preloaded assembly ensures fixed trajectories for the fixation elements 400 during delivery of the device 800 and eliminates the need for alignment post-implantation.

Figure 9:
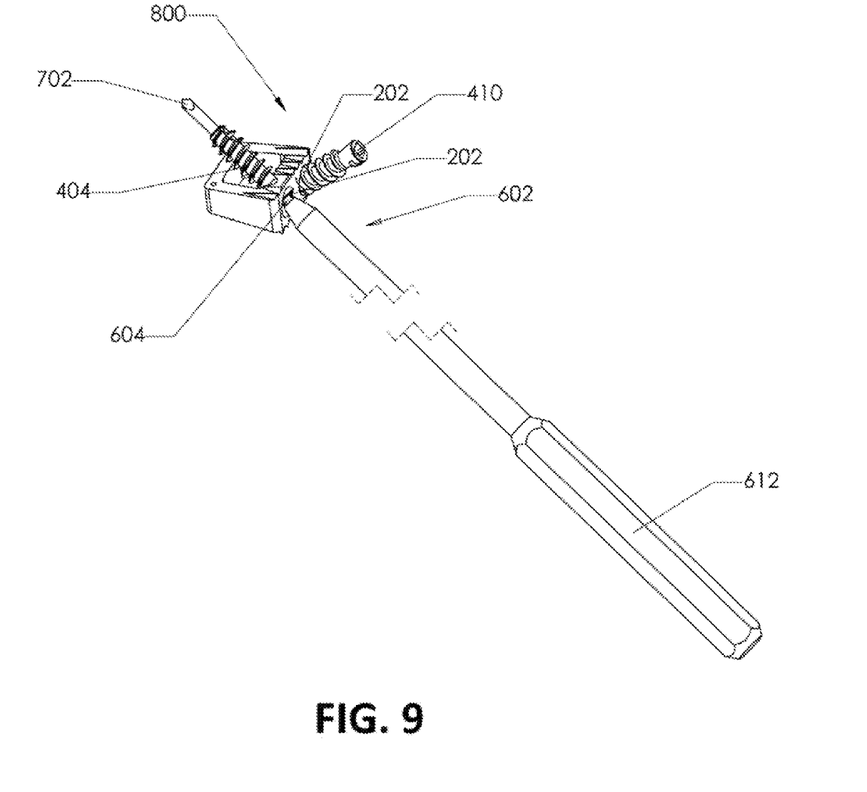
FIG. 9 is a perspective view of the example intervertebral fusion with fixation device of FIG. 8 with the example integrated drill and screwdriver of FIG. 6 actuating a fixation element shown in FIG. 4.

FIG. 9 is a perspective view of an example intervertebral fusion with fixation device of FIG. 8 with an example driving instrument 600 of FIG. 6 actuating a fixation element 400 of FIG. 4. As illustrated, the integrated tip 614 is delivered into and through the cannula 502 of the fixation element 400 to pre-drill the vertebral endplate with the cutting blades 702 of the fixation element 400. The penetration of the integrated tip 614 through the vertebral endplate combined with the linear force applied to the handle 612 drives the fixation element interface 604 into contact with the driving instrument receiver 410 of the fixation element 400. Simultaneously, the torque from the handle 612 engages the fixation element interface 604, which in turn actuates the driving instrument receiver 410 and advances the fixation element 400 into vertebral endplate. Additionally, the fixation element flutes 406 and major threading 404 penetrate and secure the fixation element 400 to the endplate of the vertebra.

Figure 10:
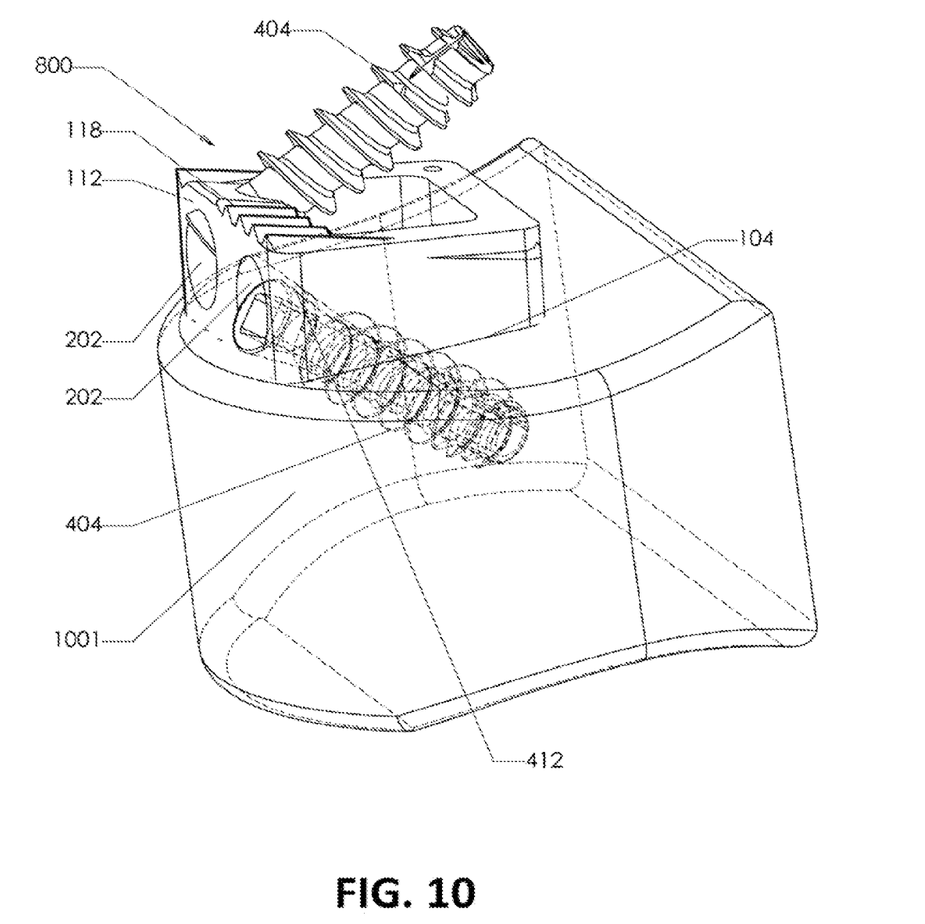
FIG. 10 is a translucent perspective view of an example intervertebral fusion with fixation device with the example fixation element of FIG. 4 in a locked position within a vertebra.

FIG. 10 is a translucent perspective view of an example intervertebral fusion with fixation device 800 with the plural example fixation elements 400 of FIG. 4 in a locked position and secured to a vertebra 1001. In a particular embodiment, the hook protrusion 412 of the fixation element 400 pressure fits the holes 202 of the spacer 100 to prevent the fixation element 400 from toggling and backing-out. Furthermore, the hook protrusion 412 rigidly cut into the spacer 100 via its sharp edge to limit the ability of the fixation element 400 to torque towards the trailing wall 112 of the device 800 and away from the vertebra 1001. Additionally, the ridges 118 penetrate adjacent vertebral endplates and provide ancillary stability.

Other apparent modifications and configurations of the invention will be appreciated by those skilled in the art to allow varying applications of the disclosed embodiments without departing from the scope of the embodiments described herein. The disclosed specifications and principles are intended to be used for illustrative purposes only, with the true scope and spirit of the patent document being defined by the following claims.

What is claimed is:

1. An intervertebral fusion with fixation device configured to be implanted between plural vertebrae, the device comprising:
   a spacer with an insertion wall, a trailing wall opposite to the insertion wall, a first lateral wall, a second lateral wall opposite to the first lateral wall, a top surface, and a bottom surface opposite to the top surface, the top and bottom surfaces each extending between the insertion wall and the trailing wall for contact with first and second vertebra respectively, wherein a first hole and a second hole extends through the spacer from the trailing wall toward the top and bottom surfaces respectively;
   a first cannulated bone screw including a first tip at a first leading end and a first head at an opposed first trailing end, the first leading end rigidly maintaining the first cannulated bone screw in a first preloaded position in the first hole along a first linear trajectory through threaded engagement of the first leading end inside the first hole, when in the first preloaded position the first tip not extending substantially above the top surface and the first head being spaced away from the spacer, the first cannulated bone screw configured to penetrate and secure to the first vertebra by advancing along the first linear trajectory to a first locked position in which the first head is advanced into the first hole; through direct engagement with a driving element and
   a second cannulated bone screw including a second tip at a second leading end and a second head at an opposed second trailing end, the second leading end rigidly maintaining the second cannulated bone screw in a second preloaded position in the second hole along a second linear trajectory that is different and divergent from the first linear trajectory through threaded engagement of the second leading end inside the second hole, when in the second preloaded position the second tip not extending substantially below the bottom surface and the second head being spaced away from the spacer, the second cannulated bone screw configured to penetrate and secure to the second vertebra by advancing along the second trajectory to a second locked position in which the second head is advanced into the second hole through direct engagement with the driving element.

2. The intervertebral fusion with fixation device of claim 1, wherein the spacer includes a through opening having an entrance proximate the top surface and an exit proximate the bottom surface to facilitate contact and in-growth of bone fusion material with the first vertebra and the second vertebra, wherein at least one of the first hole and the second hole extends to the through opening.

3. The intervertebral fusion with fixation device of claim 1, wherein the spacer is made of polyetheretherketone (PEEK), other polymers, metal, ceramics, or composites.

4. The intervertebral fusion with fixation device of claim 1, wherein the first head includes a recess for matingly receiving the driving element therein and limiting advancement of the driving element along the first trajectory.

5. The intervertebral fusion with fixation device of claim 1, wherein the first head includes a protrusion configured to penetrate and lock into the first hole to prevent screw toggling and extrusion.

6. The intervertebral fusion with fixation device of claim 1, wherein the spacer includes ridges protruding from at least one of the top surface and the bottom surface providing reinforcing structure for the first hole and the second hole.

7. The intervertebral fusion with fixation device of claim 1, wherein the first cannulated bone screw is maintained in the first preloaded position while the second cannulated bone screw is maintained in the second preloaded position.

8. An intervertebral fusion with fixation system, the system compromising:
   an intervertebral fusion with fixation device configured to be implanted between plural vertebrae, the device comprising:
      a spacer with an insertion wall, a trailing wall opposite to the insertion wall, a first lateral wall, a second lateral wall opposite to the first lateral wall, a top surface, and a bottom surface opposite to the top surface, the top and bottom surfaces each extending between the insertion wall and the trailing wall for contact with first and second vertebra respectively, wherein a first hole and a second hole extends through the spacer from the trailing wall toward the top and bottom surfaces respectively;
      a first cannulated bone screw including a first tip at a first leading end and a first head at an opposed first trailing end, the first leading end rigidly maintaining the first cannulated bone screw in a first preloaded position in the first hole along a first linear trajectory through threaded engagement of the first leading end inside the first hole, when in the first preloaded position the first tip not extending substantially above the top surface and the first head being spaced away from the spacer; and
      a second cannulated bone screw including a second tip at a second leading end and a second head at an opposed second trailing end, the second leading end rigidly maintaining the second cannulated bone screw in a second preloaded position in the second hole along a second linear trajectory that is different and divergent from the first linear trajectory through threaded engagement of the second leading end inside the second hole, when in the second preloaded position the second tip not extending substantially below the bottom surface and the second head being spaced away from the spacer, the second cannulated bone screw configured to penetrate and secure to the second vertebra by advancing along the second trajectory to a second locked position in which the second head is advanced into the second hole; and an integrated drill and screwdriver instrument, the instrument comprising:
- a drilling element configured to be inserted through a cannula of the first cannulated bone screw to penetrate the first vertebra along the first linear trajectory; and
- a driving element from which the drilling element extends, wherein the driving element is configured to engage and rotate the first cannulated bone screw from the first preloaded position into the first vertebra only after the drilling element has penetrated and advanced into the first vertebra, the driving element further rotating the first cannulated bone screw to a first locked position in which the first head is disposed in the first hole.

9. The intervertebral fusion with fixation system of claim 8, wherein the spacer includes a through opening having an entrance proximate the top surface and an exit proximate the bottom surface to facilitate contact and in-growth of bone fusion material with the first vertebra and the second vertebra, wherein at least one of the first hole and the second hole extends to the through opening.

10. The intervertebral fusion with fixation system of claim 8, wherein the first head includes a recess for matingly receiving the driving element therein and limiting advancement of the driving element along the first trajectory.

11. The intervertebral fusion with fixation system of claim 8, wherein the first head including a protrusion configured to penetrate and lock into the first hole to prevent screw toggling and extrusion.

12. The intervertebral fusion with fixation system of claim 8, wherein the threaded engagement of the first leading end cuts into the spacer inside the first hole for rigidly maintaining the first cannulated bone screw in the first preloaded position.

13. The intervertebral fusion with fixation system of claim 8, wherein the first cannulated bone screw is maintained in the first preloaded position while the second cannulated bone screw is maintained in the second preloaded position.

\* \* \* \* \*